ized by Tissot-Favre et al. US 8,742,082 B2 Date of Patent: Jun. 3, 2014

(54) COMPOSITIONS AND METHODS FOR INFLUENCING SATIETY, LIPID METABOLISM, AND FAT UTILIZATION

(75) Inventors: Delphine Tissot-Favre, Webster Groves, MO (US); Frederic Destaillats, Servion (CH); Clementine Thabuis, Wormhout (FR); Jean-Charles Martin, Marseilles (FR)

(73) Assignee: Nestec S.A., Vevey (CH)

( * ) Notice: Subject to any disclaimer, the term of this patent is extended or adjusted under 35 U.S.C. 154(b) by 428 days.

(21) Appl. No.: 12/737,744

(22) PCT Filed: Aug. 10, 2009

(86) PCT No.: PCT/US2009/004583
§ 371 (c)(1),
(2), (4) Date: Apr. 15, 2011

(87) PCT Pub. No.: WO2010/019211
PCT Pub. Date: Feb. 18, 2010

(65) Prior Publication Data
US 2011/0196042 A1 Aug. 11, 2011

Related U.S. Application Data

(60) Provisional application No. 61/188,907, filed on Aug. 14, 2008.

(51) Int. Cl.
*C12N 15/12* (2006.01)
*C12N 15/11* (2006.01)
*C07H 21/04* (2006.01)
*C07K 16/18* (2006.01)

(52) U.S. Cl.
USPC ..................... 536/23.1; 536/23.5; 530/387.1

(58) Field of Classification Search
None
See application file for complete search history.

*Primary Examiner* — James Martinell
(74) *Attorney, Agent, or Firm* — Ronald A. Burchett; Julie M. Lappin; Janet E. Reed

(57) ABSTRACT

The invention provides (1) genes differentially expressed in animals administered fatty acid amides that affect one or more of food intake, satiety, lipid metabolism, and fat utilization and (2) compositions and methods relating to the use of the genes to identify new compounds that affect one or more of food intake, satiety, lipid metabolism, and fat utilization.

17 Claims, No Drawings

US 8,742,082 B2

COMPOSITIONS AND METHODS FOR INFLUENCING SATIETY, LIPID METABOLISM, AND FAT UTILIZATION

CROSS REFERENCE TO RELATED APPLICATIONS

This application is a national stage application under 35 U.S.C. §371 of PCT/US2009/004583 filed Aug. 10, 2009, which claims priority to U.S. Provisional Application Ser. No. 61/188,907 filed Aug. 14, 2008, the disclosures of which are incorporated herein by reference.

BACKGROUND OF THE INVENTION

1. Field of the Invention

The invention relates generally to genes differentially expressed in animals and particularly to genes differentially expressed in animals administered, on a regular long-term basis, fatty acid amides that affect one or more of food intake, satiety, lipid metabolism, and fat utilization, and to the use of the differentially expressed genes to identify new compounds that affect one or more of those parameters, and to modulate the associated phenotype in an animal.

2. Description of the Related Art

Excess fat and obesity are recognized as a worldwide health problem among humans. The World Health Organization estimates that there are over 1 billion overweight adults, with just under one third of them classified as obese. In addition, obesity is also increasingly recognized as a problem for animals and particularly for companion animals such as dogs and cats. According to the Centers for Disease Control (CDC), obesity is closely associated with at least a risk of other health problems, including hypertension, dyslipidemia, Type II diabetes, heart disease, stroke, sleep apnea, and certain cancers such as breast, endometrial, and colon cancers. Risk factors for an individual becoming obese include genetics, emotions/stress, overeating and a sedentary lifestyle.

The fight against obesity began at least two decades ago with increased public communication on risks linked to excessive obesity. Nutrition recommendations have been established and re-established, widely communicated and even taught in schools. Nevertheless, the number of obese and overweight people is still increasing. In addition to healthy diet and more frequent physical activity, medicines for weight loss are now often prescribed. These medicines function on a variety of levels, including mimicking gastric fullness, reducing appetite, or limiting fat absorption. However, such drugs have not been found satisfactory for long-term treatment, due in part to decreasing effectiveness over time, as well as undesirable side effects. For at least those reasons, patient compliance with anti-obesity medications can be less than satisfactory. Clearly, there is a need in the art to discover and develop new medications or dietary supplements in the fight against obesity.

Fatty acid amides (FAEs) or N-acyl-ethanolamides are structurally related lipids that contain a fatty acid moiety linked to ethanolamine. FAEs are a family of naturally occurring lipids, found in plant and animal tissues, displaying effects on health such as the regulation of energy balance, the control of food intake and also anti-inflammatory properties. FAEs are also formed in-vivo from N-acetylated phosphatidyl-ethanolamide derivatives. The most prevalent FAEs, found in biological tissues such as brain and neuronal cells, are anandamide (N-arachidonoyl-ethanolamine) and N-oleoyl-ethanolamide (OEA). OEA is also found in foodstuffs in low amount, and mainly comes from endogenous synthesis (Di Marzo V, 1999, Life Sci. 65:645-55).

In rodents, intraperitoneal administration of OEA was reported to induce satiety and peripheral utilization of lipid substrate, thereby leading to reduced body fat gain (Thabuis C, et al, 2007, Lipid Technology 19:225-7). Both in-vitro studies and knock-out animal models have revealed some mechanisms of action, such as PPAR-alpha signaling (Fu J, et al, 2003, Nature 425:90-3), FAT/CD36-dependent lipid uptake by the proximal intestine (Yang Y, et al, 2007, Am J Physiol Regul Integr Comp Physiol. 292:R235-41), selected neuron activation (Ahern G P, 2003, J Biol Chem. 278:30429-34), and ghrelin signaling (Cani P D, et al, 2004, Br J. Nutr. 92:757-61). The proximal intestine seems to be a target organ for satiety control (Thabuis C, et al, supra). It has been shown that OEA regulates food intake in wild-type mice but not in PPAR α (−/−) mice. It has been recently shown that OEA can also bind to G-protein coupled cannabinoid receptor GPR119 (Overton H A, et al, 2006, Cell Metab. 3:167-75). When administrated intraperitoneally, OEA reduced food intake by influencing several parameters: decrease of the meal size, delay of the first meal intake and increase of meal intervals (Oveisi F, et al, 2004, Pharmacol Res. 49:461-6). The effects of OEA oral administration has been also examined 24 hours after an acute gavage administration, and has been shown to decrease significantly the food intake over the 12 first hours (Id.). However, the foregoing studies were only performed over short time periods (6 hours to 11 days for intraperitoneal administration, 24 h for oral administration), and long-term effects on satiety or other parameters relating to body fat heretofore have not been shown.

Given the problems with current methods for dealing with obesity, there is a continuing need for new methods and compositions useful for screening substances to determine if they are likely to be useful for promoting a non-obese phenotype in an animal, and using such substances to modulate the amount of adipose tissue on an animal.

SUMMARY OF THE INVENTION

It is, therefore, an object of the invention to provide one or more genes or gene segments that are differentially expressed in animals exhibiting a phenotype comprising a decrease in body fat and plasma triglycerides and an increase in satiety as measured by decreased food intake (RBF/IS phenotype) resulting from extended regular ingestion of a substance that affects one or more of food intake, satiety, lipid metabolism, and fat utilization.

It is another object of the invention to provide a combination comprising a plurality of polynucleotides that are differentially expressed in animals exhibiting a phenotype comprising a RBF/IS phenotype resulting from extended regular ingestion of a substance that affects one or more of food intake, satiety, lipid metabolism, and fat utilization.

It is another object of the invention to provide compositions of two or more polynucleotide or polypeptide probes suitable for detecting the expression of genes differentially expressed in animals exhibiting a RBF/IS phenotype resulting from extended regular ingestion of a substance that affects one or more of food intake, satiety, lipid metabolism, and fat utilization, and devices such as substrate arrays containing the probes.

It is a further object of the invention to provide methods for detecting differential expression of one or more genes differentially expressed in animals exhibiting a RBF/IS phenotype resulting from extended regular ingestion of a substance that affects one or more of food intake, satiety, lipid metabolism, and fat utilization, as compared with normal or untreated animals.

It is another object of the invention to provide a method for measuring the effect of a test substance on the expression profile of one or more genes differentially expressed in animals exhibiting a RBF/IS phenotype resulting from extended regular ingestion of a substance that affects one or more of food intake, satiety, lipid metabolism, and fat utilization, as compared with normal or untreated animals.

It is a further object of the invention to provide a method for promoting a RBF/IS phenotype in an animal.

One or more of these other objects are achieved using novel combinations of polynucleotides or polypeptides representing genes and gene segments that are differentially expressed in animals exhibiting a RBF/IS phenotype resulting from extended regular ingestion of a substance that affects one or more of food intake, satiety, lipid metabolism, and fat utilization. The polynucleotides are used to produce compositions, probes, devices based on the probes, and methods for determining the status of polynucleotides differentially expressed in animals exhibiting a RBF/IS phenotype as compared to normal or untreated animals, which are useful for achieving the above-identified objects, e.g., prognosing and diagnosing conditions relating to the phenotype and for screening substances to determine if they are likely to be useful for promoting the phenotype. Such substances, once identified, may be used to promote the phenotype. Various kits comprising combinations of probes, devices utilizing the probes, and substances are also provided, as are various computer programs for manipulating information, and communication media for communicating information pertaining to the differentially expressed genes and methods of their use.

Other and further objects, features, and advantages of the invention will be readily apparent to those skilled in the art.

DETAILED DESCRIPTION OF THE INVENTION

Definitions

All percentages expressed herein are by weight of the composition on a dry matter basis unless specifically stated otherwise. The skilled artisan will appreciate that the term "dry matter basis" means that an ingredient's concentration in a composition is measured after any free moisture in the composition is removed.

Ranges are used herein as shorthand, so as to avoid having to set out at length and describe each and every value within the range. Any appropriate value within the range can be selected, where appropriate, as the upper value, lower value, or the terminus of the range.

Dosages expressed herein are in milligrams or grams per kilogram of body weight (mg/kg or g/kg) unless expressed otherwise.

As used herein, the singular form of a word includes the plural, and vice versa, unless the context clearly dictates otherwise. Thus, the references "a," "an," and "the" are generally inclusive of the plurals of the respective terms. For example, reference to "an animal", "a method", or "a substance" includes a plurality of such "animals", "methods", or "substances". Similarly, the words "comprise", "comprises", and "comprising" are to be interpreted inclusively rather than exclusively.

The term "animal" means a human or other animal, including avian, bovine, canine, equine, feline, hicrine, murine, ovine, and porcine animals, that has adipose tissue. When the term is used in the context of comparing test subjects, the animals that are compared are animals of the same species and possibly of the same race or breed. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the animal is a human or a companion animal such as a canine or feline.

The term "antibody" means any immunoglobulin that binds to a specific antigen, including IgG, IgM, IgA, IgD, and IgE antibodies. The term includes polyclonal, monoclonal, monovalent, humanized, heteroconjugate, antibody compositions with polyepitopic specificity, chimeric, bispecific antibodies, diabodies, single-chain antibodies, and antibody fragments such as Fab, Fab', F(ab')2, and Fv, or other antigen-binding fragments.

The term "array" means an ordered arrangement of at least two probes on a substrate. At least one of the probes is a control or standard and at least one of the probes is a diagnostic probe. The arrangement of from about two to about 40,000 probes on a substrate assures that the size and signal intensity of each labeled complex formed between a probe and a sample polynucleotide or polypeptide is individually distinguishable.

The term "binding complex" refers to a complex formed when a polypeptide in a sample specifically binds (as defined herein) to a binding partner, such as an antibody or functional fragment thereof.

As used herein, a "dietary supplement" is a product that is intended to be ingested in addition to the normal diet of an animal. Dietary supplements may be in any form—e.g. solid, liquid, gel, tablets, capsules, powder, and the like. Preferably they are provided in convenient dosage forms. In some embodiments they are provided in bulk consumer packages such as bulk powders or liquids. In other embodiments, supplements are provided in bulk quantities to be included in other food items such as snacks, treats, supplement bars, beverages and the like.

The term "differential expression" or "differentially expressed" means increased or unregulated gene expression or means decreased or downregulated gene expression as detected by the absence, presence, or at least two-fold change in the amount of transcribed messenger RNA or translated protein in a sample.

The term "effective amount" means an amount of a compound, material, composition, medicament, or other material that is effective to achieve a particular biological result, such as promotion of the RBF/IS phenotype described herein.

The term "food" or "food composition" means a composition that is intended for ingestion by an animal, including a human, and provides nutrition thereto. As used herein, a "food product formulated for human consumption" is any composition specifically intended for ingestion by a human being. "Pet foods" are compositions intended for consumption by pets, preferably by companion animals. A "complete and nutritionally balanced pet food," is one that contains all known required nutrients for the intended recipient or consumer of the food, in appropriate amounts and proportions, based for example on recommendations of recognized authorities in the field of companion animal nutrition. Such foods are therefore capable of serving as a sole source of dietary intake to maintain life or promote production, without the addition of supplemental nutritional sources. Nutritionally balanced pet food compositions are widely known and widely used in the art.

The term "fragment" means (1) an oligonucleotide or polynucleotide sequence that is a portion of a complete sequence and that has the same or similar activity for a particular use as the complete polynucleotide sequence or (2) a peptide or polypeptide sequence that is a portion of a complete sequence and that has the same or similar activity for a particular use as the complete polypeptide sequence. Such fragments can comprise any number of nucleotides or amino acids deemed suitable for a particular use. Generally, oligonucleotide or polynucleotide fragments contain at least about 10, 50, 100, or 1000 nucleotides and polypeptide fragments contain at least about 4, 10, 20, or 50 consecutive amino acids from the complete sequence. The term encompasses polynucleotides and polypeptides variants of the fragments.

The term "gene" or "genes" means a complete or partial segment of DNA involved in producing a polypeptide, including regions preceding and following the coding region (leader and trailer) and intervening sequences (introns) between individual coding segments (exons). The term encompasses any DNA sequence that hybridizes to the complement of gene coding sequences.

The term "gene product" means the product of transcription of a gene, such as mRNA or derivatives thereof (e.g., cDNA), or translation of a gene transcript. The term "gene product" generally refers to the translation product, which is a protein. The term "gene product" may be used interchangeably with the term "protein" herein.

The term "homolog" means (1) a polynucleotide, including polynucleotides from the same or different animal species, having greater than 30%, 50%, 70%, or 90% sequence similarity to a reference polynucleotide, and having the same or substantially the same properties and performing the same or substantially the same function as the reference polynucleotide, or having the capability of specifically hybridizing to a reference polynucleotide under stringent conditions or (2) a polypeptide, including polypeptides from the same or different animal species, having greater than 30%, 50%, 70%, or 90% sequence similarity to a reference polypeptide and having the same or substantially the same properties and performing the same or substantially the same function as the reference polypeptide, or having the capability of specifically binding to a reference polypeptide. When referring to fragments of full length coding sequences, the function of those fragments may simply be to encode a selected portion of a polypeptide of a certain sequence, or to be of suitably similar sequence to hybridize to another polynucleotide fragment encoding that polypeptide. When referring to fragments of polypeptides, the function of those fragments may simply be to form an epitope suitable for generation of an antibody. Sequence similarity of two polypeptide sequences or of two polynucleotide sequences is determined using methods known to skilled artisans, e.g., the algorithm of Karlin and Altschul (Proc. Natl. Acad. Sci. USA 87:2264-2268 (1990)). Such an algorithm is incorporated into the NBLAST and XBLAST programs of Altschul et al. (J. Mol. Biol. 215:403-410 (1990)). To obtain gapped alignments for comparison purposes, Gapped Blast can be utilized as described in Altschul et al. (Nucl. Acids Res. 25: 3389-3402 (1997)). When utilizing BLAST and Gapped BLAST programs, the default parameters of the respective programs (e.g., XBLAST and NBLAST) are used. See http://ww.ncbi.nlm.nih.gov.

The term "hybridization complex" means a complex that is formed between sample polynucleotides when the purines of one polynucleotide hydrogen bond with the pyrimidines of the complementary polynucleotide, e.g., 5'-A-G-T-C-3' base pairs with 3'-T-C-A-G-5'. The degree of complementarily and the use of nucleotide analogs affect the efficiency and stringency of hybridization reactions.

The term "in conjunction" means that a drug, food, or other substance is administered to an animal (1) together in a composition, particularly food composition, or (2) separately at the same or different frequency using the same or different administration routes at about the same time or periodically. "Periodically" means that the substance is administered on a dosage schedule acceptable for a specific substance. "About the same time" generally means that the substance (food or drug) is administered at the same time or within about 72 hours of each other. "In conjunction" specifically includes administration schemes wherein substances such as drugs are administered for a prescribed period and compositions of the invention are administered indefinitely.

The term "individual" when referring to an animal means an individual animal of any species or kind.

"Long term" administration as used herein generally refers to periods in excess of one month. Periods of longer than two, three, or four months are contemplated. Also included are more extended periods that include longer than 5, 6, 7, 8, 9, or 10 months. Periods in excess of 11 months or 1 year are also included. Longer terms use extending over 1, 2, 3, or more years are also contemplated herein. In the case of certain animals, it is envisioned that the animal would be administered substances identified by the present methods on a regular basis. "Regular basis" as used herein refers to at least weekly, administration. More frequent administration, such as twice or thrice weekly is contemplated. Also included are regimens that comprise at least once, twice, three times or more daily administration. Any dosing frequency, regardless of whether expressly exemplified herein, is considered useful. The skilled artisan will appreciate that dosing frequency will be a function of the substance that is being administered, and some compositions may require more or less frequent administration to maintain a desired biochemical, physiological or gene expression effects, namely effects including one or more of food intake, satiety, lipid metabolism, and fat utilization, and the gene expression profile associated therewith. The term "extended regular basis" refers to long term administration of a substance on a regular basis.

"Normal" or "normal subjects" or "normal animals" as used in relation to subjects manifesting a RBF/IS phenotype, refers to the absence of molecular, biochemical, physiologic, cellular, systemic, and physical effects resulting from the differential expression of genes associated with the RBF/IS phenotype.

The term "oral administration" or "orally administering" means that the animal ingests, or a human is directed to feed, or does feed, the animal one or more of the substances described herein. The term "ingestion" is used herein interchangeably with the term "oral administration." Wherein a human is directed to orally administer or feed the substance, such direction may be that which instructs and/or informs the human that use of the substance may and/or will provide the referenced benefit. Such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., interne, electronic mail, or other computer-related media), and/or packaging associated with the substance.

The term "polynucleotide" or "oligonucleotide" means a polymer of nucleotides. The term encompasses DNA and RNA (including cDNA and mRNA) molecules, either single or double stranded and, if single stranded, its complementary sequence in either linear or circular form. The term also encompasses fragments, variants, homologs, and alleles, as appropriate for the sequences, which have the same or substantially the same properties and perform the same or substantially the same function as the original sequence. In particular, the term encompasses homologs from different species, e.g., a mouse and a dog or cat. The sequences may be fully complementary (no mismatches) when aligned or may have up to about a 30% sequence mismatch. Preferably, for polynucleotides, the chain contains from about 50 to 10,000 nucleotides, more preferably from about 150 to 3,500 nucleotides. Preferably, for oligonucleotides, the chain contains from about 2 to 100 nucleotides, more preferably from about 6 to 30 nucleotides. The exact size of a polynucleotide or oligonucleotide will depend on various factors and on the particular application and use of the polynucleotide or oligonucleotide. The term includes nucleotide polymers that are synthesized and that are isolated and purified from natural sources. The term "polynucleotide" is inclusive of "oligonucleotide."

The term "polypeptide," "peptide," or "protein" means a polymer of amino acids. The term encompasses naturally occurring and non-naturally occurring (synthetic) polymers and polymers in which artificial chemical mimetics are substituted for one or more amino acids. The term also encompasses fragments, variants, and homologs that have the same or substantially the same properties and perform the same or substantially the same function as the original sequence. The term encompass polymers of any length, preferably polymers containing from about 2 to 1000 amino acids, more preferably from about 5 to 500 amino acids. The term includes amino acid polymers that are synthesized and that are isolated and purified from natural sources.

The term "probe" means (1) an oligonucleotide or polynucleotide, either RNA or DNA, whether occurring naturally as in a purified restriction enzyme digest or produced synthetically, that is capable of annealing with or specifically hybridizing to a polynucleotide with sequences complementary to the probe or (2) a compound or substance, including a peptide or polypeptide, capable of specifically binding a particular protein or protein fragment to the substantial exclusion of other proteins or protein fragments. An oligonucleotide or polynucleotide probe may be either single or double stranded. The exact length of the probe will depend upon many factors, including temperature, source, and use. For example, for diagnostic applications, depending on the complexity of the target sequence, an oligonucleotide probe typically contains about 10 to 100, 15 to 50, or 15 to 25 nucleotides. In certain diagnostic applications, a polynucleotide probe contains about 100-1000, 300-600, nucleotides, preferably about 300 nucleotides. The probes herein are selected to be "substantially" complementary to different strands of a particular target sequence. This means that the probes must be sufficiently complementary to specifically hybridize or anneal with their respective target sequences under a set of predetermined conditions. Therefore, the probe sequence need not reflect the exact complementary sequence of the target. For example, a noncomplementary nucleotide fragment may be attached to the 5' or 3' end of the probe, with the remainder of the probe sequence being complementary to the target sequence. Alternatively, noncomplementary bases or longer sequences can be interspersed into the probe provided that the probe sequence has sufficient complementarity with the sequence of the target polynucleotide to specifically anneal to the target polynucleotide. A peptide or polypeptide probe may be any molecule to which the protein or peptide specifically binds, including DNA (for DNA binding proteins), antibodies, cell membrane receptors, peptides, cofactors, lectins, sugars, polysaccharides, cells, cell membranes, organelles and organellar membranes.

The term "sample" means any animal tissue or fluid containing, e.g., polynucleotides, polypeptides, antibodies, metabolites, and the like, including cells and other tissue containing DNA and RNA. Examples include adipose, blood, cartilage, connective, epithelial, lymphoid, muscle, nervous, sputum, and the like. A sample may be solid or liquid and may be DNA, RNA, cDNA, bodily fluids such as blood or urine, cells, cell preparations or soluble fractions or media aliquots thereof, chromosomes, organelles, and the like.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use.

The term "specifically bind" means a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

The term "specifically hybridize" means an association between two single stranded polynucleotides of sufficiently complementary sequence to permit such hybridization under predetermined conditions generally used in the art (sometimes termed "substantially complementary"). For example, the term may refer to hybridization of a polynucleotide probe with a substantially complementary sequence contained within a single stranded DNA or RNA molecule according to an aspect of the invention, to the substantial exclusion of hybridization of the polynucleotide probe with single stranded polynucleotides of non-complementary sequence.

The term "standard" means (1) a control sample that contains tissue from a subject administered a control or reference substance, or no substance, as compared with a sample that contains tissue from a subject administered a test substance, for example, to determine if the test substance causes differential gene expression, as appropriate for the context of its use.

The term "stringent conditions" means (1) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C., (2) hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C.; with washes at 42° C. in 0.2×SSC and 0.1% SDS or washes with 0.015 M NaCl, 0.0015 M sodium citrate, 0.1% Na2SO4 at 50° C. or similar procedures employing similar low ionic strength and high temperature washing agents and similar denaturing agents.

The term "variant" means (1) a polynucleotide sequence containing any substitution, variation, modification, replacement, deletion, or addition of one or more nucleotides from or to a polynucleotide sequence and that has the same or substantially the same properties and performs the same or substantially the same function as the original sequence and (2) a polypeptide sequence containing any substitution, variation, modification, replacement, deletion, or addition of one or more amino acids from or to a polypeptide sequence and that has the same or substantially the same properties and performs the same or substantially the same function as the original sequence. The term therefore includes single nucleotide polymorphisms (SNPs) and allelic variants and includes conservative and non-conservative amino acid substitutions in polypeptides. The term also encompasses chemical derivatization of a polynucleotide or polypeptide and substitution of nucleotides or amino acids with nucleotides or amino acids that do not occur naturally, as appropriate.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to and does not limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the invention, the preferred compositions, methods, articles of manufacture, or other means or materials are described herein.

All patents, patent applications, publications, and other references cited or referred to herein are incorporated herein by reference to the extent allowed by controlling law. The discussion of those references is intended merely to summarize the assertions made therein. No admission is made that any such patents, patent applications, publications or references, or any portion thereof, is relevant, material, or prior art. The right to challenge the accuracy and pertinence of any assertion of such patents, patent applications, publications, and other references as relevant, material, or prior art is specifically reserved.

THE INVENTION

The invention arises in part from a clear demonstration that fatty acid amides known to affect food intake, satiety, lipid metabolism, and/or fat utilization when administered peritoneally, cause decreased body fat and plasma triglyceride levels, increased satiety as measured by decreased food intake, and a concomitant change in expression of several genes associated with body fat mass and food intake, when orally administered on an extended regular basis. Namely, as exemplified herein, supplementation with OEA at two different concentrations significantly lowered food intake, decreased adipose tissue mass and lowered plasma triglycerides over a four-week test period in an animal model. The expression of 44 genes related to body fat mass and food intake was measured by real-time PCR in peripheral tissues of subjects administered OEA or a hydrolysis-resistant derivative thereof, over a multi-week test period. The gene products of the differentially expressed genes are set forth herein in Table 1 and Table 2. Multivariate statistical analysis showed a significant shift in the overall gene expression pattern resulting from these treatments. In particular, the genes of adipose leptin and FAAH (fatty acid amide hydrolysis), intestinal FAT/CD36 and OEA receptor GPR119 were among the genes responsible for the shift. Statistical correlation analysis showed those genes to be associated with reduced adipose pads, while adipose FAAH was found to be mainly associated with a decrease in food intake.

The proteins set forth in Table 1 and Table 2 are divided into groups based upon different criteria. First, the proteins are divided into four groups based upon a statistical analysis of the differential expression of each gene in treated versus untreated animals. The first "group" encompasses all proteins listed in Table 1 and Table 2. The second group, Group A, represents proteins in which the difference in gene expression between treated and untreated animals was statistically significant at the $p<0.05$ level. The third group, Group B, represents proteins in which the difference in gene expression between treated and untreated animals was statistically significant at the $p<0.01$ level. The fourth group, Group C, represents proteins in which the difference in gene expression between treated and untreated animals was statistically significant at the $p<0.001$ level.

Second, the proteins are divided into a group based upon the function or physiological role of the protein. Those functions include: lipid β-oxidation, lipogenesis, lipid transport, insulin signaling, control of food intake, fatty acid ethanolamide metabolism or signaling, and glucose metabolism.

Thus, a number of genes have been identified that are differentially expressed in subjects manifesting a decrease in body fat and plasma triglycerides and an increase in satiety as measured by decreased food intake (referred to herein as a reduced body fat/increased satiety (RBF/IS) phenotype), all resulting from long-term regular ingestion of substances, namely OEA and derivatives thereof, which affect food intake, satiety, lipid metabolism, and/or fat utilization. Polynucleotides and fragments thereof that form these genes, as well as their encoded proteins and fragments, can be used, for example, in diagnostic or prognostic assays to measure a shift to a RBF/IS phenotype, or assays useful for screening test compounds for their effectiveness to promote or support a RBF/IS phenotype.

In certain embodiments of the invention, expression of at least one differentially expressed gene may be measured. In preferred embodiments, expression of two or more differentially expressed genes may be measured, providing a gene expression pattern or gene expression profile. More preferably, measurement of a multiplicity of differentially expressed genes may be performed, providing additional information for a gene expression pattern or profile.

In various embodiments of the invention, changes in gene expression may be measured in one or both of two ways: (1) measuring transcription through detection of mRNA produced by a particular gene; and (2) measuring translation through detection of protein produced by a particular transcript.

Decreased or increased expression can be measured at the RNA level using any of the methods well known in the art for the quantization of polynucleotides, such as, for example, PCR (including, without limitation, RT-PCR and qPCR), RNase protection, Northern blotting, microarray, macroarray, and other hybridization methods. The genes that are assayed or interrogated according to the invention are typically in the form of mRNA or reverse transcribed mRNA. The genes may be cloned and/or amplified. The cloning itself does not appear to bias the representation of genes within a population. However, it may be preferable to use polyA+ RNA as a source, as it can be used with fewer processing steps.

Thus, one aspect of the invention provides a combination comprising a plurality of polynucleotides or proteins expressed therefrom that are differentially expressed in animals exhibiting a RBF/IS phenotype as a result of extended regular administration of substance that affects one or more of food intake, satiety, lipid metabolism, and fat utilization, wherein the polynucleotides are selected from genes encoding proteins listed in Table 1 or Table 2, or fragments thereof. In one embodiment, the polynucleotides or expressed proteins are selected from genes encoding proteins listed in Group A of Table 1 or Table 2, or fragments thereof. In another embodiment, the polynucleotides or expressed proteins are selected from genes encoding proteins listed in Group B of Table 1 or Table 2, or fragments thereof. In another embodiment, the polynucleotides or expressed proteins are selected from genes encoding proteins listed in Group C of Table 1 or Table 2, or fragments thereof. In another embodiment, the polynucleotides or expressed proteins are selected from genes encoding proteins involved one or more of the following functions: lipid β-oxidation, lipogenesis, lipid transport, insulin signaling, control of food intake, fatty acid ethanolamide metabolism or signaling, and glucose metabolism.

In one embodiment, the combination comprises two or more polynucleotides or proteins expressed from the polynucleotides. Preferably, the combination comprises a plurality of polynucleotides or proteins expressed from polynucleotides, generally about 5, 10, 15, 20, 25, 30, 35, 40, 45, 50, 60, 70, 80, 90, 100 or more polynucleotides or proteins, or fragments thereof, as appropriate for a particular Group and use. When the combination comprises one or more fragments, the fragments can be of any size that retains the properties and function of the original polynucleotide or protein, preferably from about 30%, 60%, or 90% of the original.

The polynucleotides and proteins can be from any animal, preferably canines and felines, most preferable canines. Homologs of the polynucleotides and proteins from different animal species are obtainable by standard information mining and molecular methods well known to the skilled artisan. For example, the name, or description of function of a gene or protein may be entered into one of several publicly available databases, which will generate a list of sources providing information about that gene from different species, including sequence information. One such database is the "Information Hyperlinked over Proteins (iHOP) database, which is accessible on the internet via the url: ihop-net.org. Alternatively, a public database accession number of a known gene or protein may be utilized to access sequence information for that gene or protein and to search for homologs or orthologs in other species using a sequence comparison search. For example, the GenBank accession number of a gene or protein from mouse may be entered into the National Institutes of Health's National Center for Biotechnology Information (NCBI) database, thereby accessing DNA or polypeptide sequences for that mouse gene. Using the same database, a BLAST search may be performed on the mouse DNA or protein sequence, or fragments thereof of sufficient length to define the gene or protein, to identify sequences of sufficient homology from other species, e.g., a canine. Accession numbers of the sequences from the other species of interest may then be entered into the database to obtain information pertaining to those full-length nucleotide or protein sequences, as well as other descriptive information.

Another aspect of the invention provides a composition comprising two or more probes for detecting differential gene expression in animals exhibiting a RBF/IS phenotype as a result of regular extended ingestion of a substance that affects one or more of food intake, satiety, lipid metabolism, and fat utilization. The probes may comprise polynucleotides or oligonucleotides that specifically hybridize with genes encoding the proteins listed in Table 1 or Table 2, or fragments thereof. Alternatively, they may comprise polypeptide binding agents that specifically bind to polypeptides comprising the proteins listed in Table 1 or Table 2, or fragments thereof. In certain embodiments, the polypeptide binding agents are antibodies, and in a particular embodiment they are monoclonal antibodies. In one embodiment, the probes specifically hybridize to genes encoding proteins listed in Group A of Table 1 or Table 2, or fragments thereof, or they specifically bind to polypeptides comprising proteins listed in Group A of Table 1 or Table 2, or fragments thereof. In another embodiment, the probes specifically hybridize to genes encoding proteins listed in Group B of Table 1 or Table 2, or fragments thereof, or they specifically bind to polypeptides comprising proteins listed in Group B of Table 1 or Table 2, or fragments thereof. In yet another embodiment, the probes specifically hybridize to genes encoding proteins listed in Group C of Table 1 or Table 2, or fragments thereof, or they specifically bind to polypeptides comprising proteins listed in Group C of Table 1 or Table 2, or fragments thereof. In another embodiment, the probes specifically hybridize to, or specifically bind to, polynucleotides encoding proteins, or polypeptides comprising proteins, which have a function selected from: lipid β-oxidation, lipogenesis, lipid transport, insulin signaling, control of food intake, fatty acid ethanolamide metabolism or signaling, and glucose metabolism. In a preferred embodiment, the probes specifically hybridize or bind to canine or feline polynucleotides or polypeptides.

Preferably, the composition comprises a plurality of probes, generally about 5, 10, 15, 20, 25, 30, 35, 40, 45, 50, 60, 70, 80, 90, 100, 200, 500 or more probes for detecting the polynucleotides or proteins, or fragments thereof, as appropriate for a particular Group and use. It will be understood by the skilled artisan that multiple different probes for a single target gene or protein may be utilized, to refine the sensitivity or accuracy of an assay utilizing the probes. For example, several oligonucleotide probes, specifically hybridizing to different sequences on a target polynucleotide, may be employed. Likewise, several antibodies, immunologically specific for different epitopes on a target protein, may be utilized.

One or more oligonucleotide or polynucleotide probes for interrogating a sample may be prepared using the sequence information for any of the genes listed herein, from any species, preferably canine or feline. The probes should be of sufficient length to specifically hybridize substantially exclusively with appropriate complementary genes or transcripts. In certain embodiments, the oligonucleotide probes will be at least about 10, 12, 14, 16, 18, 20 or 25 nucleotides in length. In some embodiments, longer probes of at least about 30, 40, 50, 60, 70, 80, 90 or 100 nucleotides are desirable, and probes longer than about 100 nucleotides may be suitable in some embodiments. The probes may comprise full length sequences encoding functional proteins. The nucleic acid probes are made or obtained using methods known to skilled artisans, e.g., in vitro synthesis from nucleotides, isolation and purification from natural sources, or enzymatic cleavage of the polynucleotides of the invention.

Hybridization complexes comprising nucleic acid probes hybridized to a polynucleotide of the invention may be detected by a variety of methods known in the art. In certain embodiments of the invention, immobilized nucleic acid probes may be used for the rapid and specific detection of polynucleotides and their expression patterns. Typically, a nucleic acid probe is linked to a solid support and a target polynucleotide (e.g., a gene, a transcription product, an amplicon, or, most commonly, an amplified mixture) is hybridized to the probe. Either the probe, or the target, or both, can be labeled, typically with a fluorophore or other tag, such as streptavidin. Where the target is labeled, hybridization may be detected by detecting bound fluorescence. Where the probe is labeled, hybridization is typically detected by quenching of the label. Where both the probe and the target are labeled, detection of hybridization is typically performed by monitoring a color shift resulting from proximity of the two bound labels. A variety of labeling strategies, labels, and the like, particularly for fluorescent based applications, are known in the art.

In another embodiment, the probes comprise polypeptide binding agents that specifically bind to polypeptides produced by expression of one or more of the polypeptides listed herein, or fragments thereof. Such protein binding probes may be prepared using the sequence information available for any of the proteins identified in Table and Table 2, or fragments thereof.

Assay techniques that can be used to determine levels of a protein in a sample are also well known to those of skill in the art. Such assay methods include radioimmunoassays, competitive-binding assays, Western blot analysis and ELISA assays. In the assay methods utilizing antibodies, both polyclonal and monoclonal antibodies are suitable for use in the invention. Such antibodies may be immunologically specific for a particular protein, or an epitope of the protein, or a protein fragment, as would be well understood by those of skill in the art. Methods of making polyclonal and monoclonal antibodies immunologically specific for a protein or peptide are also well known in the art.

Preferred embodiments of the invention may utilize antibodies for the detection and quantification of proteins produced by expression of the genes described herein. Though proteins may be detected by immunoprecipitation, affinity separation, Western blot analysis and the like, a preferred method utilizes ELISA-type methodology wherein the antibody is immobilized on a solid support and a target protein or peptide is exposed to the immobilized antibody. Either the probe, or the target, or both, can be labeled. A variety of labeling strategies, labels, and the like, are known in the art.

Another aspect of the invention provides a device comprising a solid support to which is affixed an array comprising a plurality of probes for detecting differential gene expression in animals exhibiting a RBF/IS phenotype due to extended regular ingestion of a substance that affects one or more of food intake, satiety, lipid metabolism, and fat utilization. In particularly preferred embodiments of the invention, expression patterns or profiles of a plurality of genes differentially expressed RBF/IS versus normal phenotypes as defined herein, are observed utilizing arrays of probes for detecting target polynucleotides or proteins. The device may be used to detect differential expression of genes encoding the gene products set forth in Table 1 or table 2, or in subsets thereof, namely Group A, Group B, Group C, or functional subsets including functions selected from: lipid β-oxidation, lipogenesis, lipid transport, insulin signaling, control of food intake, fatty acid ethanolamide metabolism or signaling, and glucose metabolism. In a preferred embodiment, the device is uses to detect differential expression of genes from canines or felines.

In one embodiment, arrays of oligonucleotide or polynucleotide probes may be utilized, whereas another embodiment may utilize arrays of antibodies or other proteins that bind specifically to the differentially expressed gene products. Such arrays may be custom made according to known methods, such as, for example, in-situ synthesis on a solid support or attachment of pre-synthesized probes to a solid support via micro-printing techniques. In preferred embodiments, arrays of nucleic acid or protein-binding probes are custom made to specifically detect transcripts or proteins produced by two or more of the differentially expressed genes or gene fragments described herein.

Another aspect of the invention provides a method for detecting differential expression of one or more genes differentially expressed in animals exhibiting a phenotype comprising a decrease in body fat and plasma triglycerides and an increase in satiety as measured by decreased food intake (RBF/IS phenotype) resulting from extended regular ingestion of a substance that affects one or more of food intake, satiety, lipid metabolism, and fat utilization, as compared with normal or untreated animals. The method generally comprises: (a) providing probes comprising (i) polynucleotides that specifically hybridize to two or more genes encoding proteins listed in Table 1 or Table 2, or fragments thereof; or (ii) polypeptide binding agents that specifically bind to two or more polypeptides selected from proteins listed in Table 1 or Table 2, or fragments thereof; (b) adding the probes to a sample comprising mRNA or proteins from an animal exhibiting the RBF/IS phenotype, in a manner enabling hybridization or binding of the probes to the mRNA or proteins in the sample, thereby forming hybridization or binding complexes in the sample (c) optionally, adding the probes to another sample comprising mRNA or proteins from a normal animal, in a manner enabling hybridization or binding of the probes to the mRNA or proteins in the second sample, thereby forming hybridization or binding complexes in the other sample; (d) detecting the hybridization complexes in the sample or samples; and (e) comparing the hybridization or binding complexes from the first sample with the hybridization or binding complexes from a standard or, optionally, from the other sample, wherein at least one difference between the amount of hybridization or binding in the sample as compared with the standard or the optional other sample indicates differential expression of the one or more genes differentially expressed in animals exhibiting the RBF/IS phenotype, as compared to animals that do not exhibit the phenotype.

The method may be used to detect differential expression of genes encoding the gene products set forth in Table 1 or table 2, or in subsets thereof, namely, Group A, Group B, Group C, or functional subsets including functions selected from: lipid β-oxidation, lipogenesis, lipid transport, insulin signaling, control of food intake, fatty acid ethanolamide metabolism or signaling, and glucose metabolism. In a preferred embodiment, the method is used to detect differential expression of genes from canines or felines. In particular embodiments, the probes are bound to a substrate, preferably in an array.

Step (c) and part of steps (d) and (e) are optional and are used if a relatively contemporaneous comparison of two or more test systems is to be conducted. However, in a preferred embodiment, the standard used for comparison is based upon data previously obtained using the method.

These probes are exposed to a sample to form hybridization or binding complexes that are detected and compared with those of a standard. The differences between the hybridization or binding complexes from the sample and standard indicate differential expression of polynucleotides and therefore genes differentially expressed in RBF/IS phenotype versus normal phenotype in the sample. In a preferred embodiment, probes are made to specifically detect polynucleotides or fragments thereof produced by one or more of the genes or gene fragments identified by the invention. Methods for detecting hybridization complexes are known to skilled artisans.

In one embodiment, the method further comprises exposing the animal or sample to a test substance before performing the assay. Then, the comparison is indicative of whether the test substance altered the expression of genes differentially expressed in treated versus untreated animals.

In another embodiment useful for diagnostic or prognostic determination of the RBF/IS phenotype, the detecting is performed at intervals, for example, to monitor an animal's progress when attempting to induce the RBF/IS phenotype in the animal.

Another aspect of the invention provides a method of determining if a test substance is likely to be useful in affecting one or more of food intake, satiety, lipid metabolism, and fat utilization, thereby inducing a RBF/IS phenotype when administered to an animal on a regular extended basis. The method typically comprises (a) determining a first gene expression profile by measuring the transcription or translation products of two or more polynucleotides selected from genes encoding proteins listed in Table 1 or Table 2, or fragments thereof, in a test system in the absence of the test substance; (b) determining a second gene expression profile by measuring the transcription or translation products of two or more polynucleotides selected from genes encoding proteins listed in Table 1 or Table 2, or fragments thereof, in a test system in the presence of the test substance; and (c) comparing the first gene expression profile with the second gene expression profile, wherein a change in the second gene expression profile as compared with the first gene expression profile indicates that the test substance is likely to be useful in affecting one or more of food intake, satiety, lipid metabolism, and fat utilization when administered to an animal.

In certain embodiments, the method may further include the step of comparing at least the second gene expression profile with a reference or standard gene expression profile obtained by measuring the transcription or translation products of two or more polynucleotides selected from genes encoding proteins listed in Table 1 or Table 2, or fragments thereof, in a test system in the presence of a reference substance known to affect one or more of food intake, satiety, lipid metabolism and fat utilization when administered to animals. Such a substance may be, for example, OEA or a hydrolysis-resistant derivative thereof.

In one embodiment, the test system comprises a population of cultured cells. A nucleic acid construct comprising a RBF/IS associated gene according to the invention is introduced into cultured host cells. The host cells can be mammalian cell lines, such as but are not limited to, NIH3T3, CHO, HELA, and COS, although non-mammalian cells such as yeast, bacteria and insect cells can also be used. The coding sequences of the genes are operably linked to appropriate regulatory expression elements suitable for the particular host cell to be utilized. The nucleic acid constructs can be introduced into the host cells according to any acceptable means in the art, including but not limited to, transfection, transformation, calcium phosphate precipitation, electroporation and lipofection. Such techniques are well known and routine in the art. Transformed cells can be also used to identify compounds that modulate expression of the RBF/IS-associated genes.

Gene expression assays can be carried out using a gene construct comprising the promoter of a selected RBF/IS-associated gene operably linked to a reporter gene. The reporter construct may be introduced into a suitable cultured cell, including, without limitation, the standard host cell lines described above, or cells freshly isolated from a subject such as adipose, muscle, or liver cells. The assay is performed by monitoring expression of the reporter gene in the presence or absence of a test compound.

In a preferred embodiment, the test system comprises animals. Typically, a test compound is administered to a subject and the gene expression profile of the subject is analyzed to determine the effect of the test compound on transcription or the translation of the genes or gene products of the invention. Gene expression can be analyzed in situ or ex vivo to determine the effect of the test compound. In another embodiment, a test compound is administered to a subject and the activity of a protein expressed from a gene is analyzed in situ or ex vivo according to any means suitable in the art to determine the effect of the test compound on the activity of the proteins of interest. In addition, where a test compound is administered to a subject, the physiological, systemic, and physical effects of the compound, as well as potential toxicity of the compound can also be evaluated.

Test substances can be any substance that may have an effect on polynucleotides or genes differentially expressed in animals exhibiting a RBF/IS phenotype. Preferred test substances are fatty acid amides, such as derivatives of OEA. Other test substances include, but are not limited to, amino acids; proteins, peptides, polypeptides, nucleic acids, oligonucleotides, polynucleotides, small molecules, macromolecules, vitamins, minerals, simple sugars; complex sugars; polysaccharides; carbohydrates; medium-chain triglycerides (MCTs); triacylglycerides (TAGs); n-3 (omega-3) fatty acids including DHA, EPA, ALA; n-6 (omega-6) fatty acids including LA, γ-linolenic acid (GLA) and ARA; SA, conjugated linoleic acid (CLA); choline sources such as lecithin; fat-soluble vitamins including vitamin A and precursors thereof such as carotenoids (e.g., (β-carotene), vitamin D sources such as vitamin D2 (ergocalciferol) and vitamin D3 (cholecalciferol), vitamin E sources such as tocopherols (e.g., α-tocopherol) and tocotrienols, and vitamin K sources such as vitamin K1 (phylloquinone) and vitamin K2 (menadione); water-soluble vitamins including B vitamins such as riboflavin, niacin (including nicotinamide and nicotinic acid), pyridoxine, pantothenic acid, folic acid, biotin and cobalamin; and vitamin C (ascorbic acid); antioxidants, including some of the vitamins listed above, especially vitamins E and C; also bioflavonoids such as catechin, quercetin and theaflavine; quinones such as ubiquinone; carotenoids such as lycopene and lycoxanthin; resveratrol; and α-lipoic acid; L-carnitine; D-limonene; glucosamine; S-adenosylmethionine; and chitosan. In a preferred embodiment, test substances are nutrients that may be added to food or consumed as a supplement.

Substances identified by the foregoing method are also contemplated as part of the invention.

Another aspect of the invention provides a method of promoting a RBF/IS phenotype in an animal. The method comprises orally administering to the animal, on an extended regular basis, a substance that affects one or more of food intake, satiety, lipid metabolism, and fat utilization. Preferably, the animal is a canine or a feline. Typically the substance is regularly administered for at least two weeks, more preferably for at least four weeks or longer. Administration of the substance may continue indefinitely, e.g., for one, two, three, six or nine months, or for a year or more, or even for the life of the animal. The substance generally is administered at least daily, but the dosage regimen will depend on the nature and potency of the substance. Accordingly, administration may be more frequent, e.g., twice or three times daily, or less frequent, e.g., three times weekly, twice weekly, weekly, twice monthly or monthly.

In certain embodiments, the substance is a fatty acid amide. In particular, the substance is N-oleoyl-ethanolamide or a hydrolysis-resistant derivative thereof, such as (Z)—(R)-9-octadecena-mide, N-(2-hydroxyethyl, 1-methyl). In other embodiments, the substance is a substance identified by the screening method described hereinabove.

In certain embodiments, the extended regular oral administration of the substance causes a change in expression of one or more genes of Table 1 or Table 2. In specific embodiments, the extended regular oral administration of the substance causes a change in expression of one or more genes encoding proteins selected from leptin, fatty acid amide hydrolysis (FAAH), FAT/CD36 and oleoyl-ethanolamide receptor GPR119.

When utilized as a supplement to ordinary dietetic requirements, the substance may be administered directly to the animal. The substance can alternatively be contacted with, or admixed with, daily feed or food, including a fluid, such as drinking water, or supplied as a dietary supplement. When utilized in conjunction with or incorporated into a daily feed or food, administration will be well known to those of ordinary skill. Administration can be carried out as part of a dietary regimen for the animal. For example, a dietary regimen may comprise causing the regular ingestion by the animal of the substance, in an amount effective to promote the RBF/IS phenotype. In another embodiment, the substance is administered to the animal in conjunction with one or more drugs, nutraceuticals, or nutritional agents for the modulation of body fat or the promotion of a RBF/IS phenotype in the animal.

In certain embodiments, daily or periodic doses for the substance administered in accordance with this method range from about 0.001 g/kg body weight to 10 g/kg body weight. More particularly, the dose exceeds 0.01, 0.02, 0.03, 0.04, 0.05, 0.06, 0.07, 0.08, 0.09 or 0.1 g/kg body weight. In other embodiments, the dosage may be 0.2, 0.5, 1, 3, 5, 7, or 10 g/kg body weight or more, depending on the substance and dosing frequency. The skilled artisan is familiar with the development of dosages and dosing regimens for subjects.

Another aspect of the invention provides a computer system comprising a database containing information identifying expression levels of one or more polynucleotides that are differentially expressed in animals administered a substance that affects one or more of food intake, satiety, lipid metabolism, and fat utilization, wherein the polynucleotides are selected from genes encoding proteins listed in Table 1 or Table 2, or fragments thereof, and a user interface that enables a user to access or manipulate the information in the database. The system comprises a database containing information identifying the expression level of one or more polynucleotides selected from genes encoding proteins listed in Table 1 or Table 2 and/or polypeptides that specifically bind to the proteins listed in Table 1 or Table 2, and a user interface to interact with the database, particularly to input, manipulate, and review the information for different animals or categories of animals. In one embodiment, the database further contains information identifying the activity level of one or more polypeptides listed in Table 1 or Table 2. In another, the database further comprises sequence information for one or more of the polynucleotides or polypeptides as listed in Table 1 or Table 2, preferably from a variety of species. In other embodiments, the database contains additional information describing the putative description of the genes in one or more animal species. The computer system is any electronic device capable of containing and manipulating the data and interacting with a user, e.g., a typical computer or an analytical instrument designed to facilitate using the invention and outputting the results relating to the status of an animal.

In another aspect, the invention provides a kit comprising a container containing a collection of two or more probes for detecting differential gene expression of the RBF/IS phenotype resulting from regular extended ingestion of a substance that affects one or more of food intake, satiety, lipid metabolism, and fat utilization. The kits comprise in separate containers in a single package or in separate containers in a virtual package, as appropriate for the use and kit component, two or more probes for detecting differential gene expression in animals exhibiting a phenotype comprising a decrease in body fat and plasma triglycerides and an increase in satiety as measured by decreased food intake (RBF/IS phenotype) resulting from extended regular ingestion of a substance that affects one or more of food intake, satiety, lipid metabolism, and fat utilization, wherein the probes comprise: (a) polynucleotides that specifically hybridize to two or more genes encoding proteins listed in Table 1 or Table 2, or fragments thereof; or (b) polypeptide binding agents that specifically bind to two or more polypeptides selected from proteins listed in Table 1 or Table 2, or fragments thereof; and further comprises at least one of (1) instructions for how to use the probes in a gene expression assay for detecting differential gene expression in animals exhibiting a phenotype comprising a decrease in body fat and plasma triglycerides and an increase in satiety as measured by decreased food intake (RBF/IS phenotype) resulting from extended regular ingestion of a substance that affects one or more of food intake, satiety, lipid metabolism, and fat utilization, (2) reagents and equipment for using the probes, and (3) a composition known to induce the RBF/IS phenotype upon regular extended ingestion. Preferably, the probes are affixed to a solid support at known locations. Suitable reference substances known to induce the RBF/IS phenotype upon regular ingestion are N-oleoyl-ethanolamide or hydrolysis-resistant derivatives thereof.

When the kit comprises a virtual package, the kit is limited to instructions in a virtual environment in combination with one or more physical kit components. In one embodiment, the kit contains probes and/or other physical components and the instructions for using the probes and other components are available via the Internet. The kit may contain additional items such as a device for mixing samples, probes, and reagents and device for using the kit, e.g., test tubes or mixing utensils.

In another aspect, the invention provides a means for communicating information about or instructions for one or more of compositions and methods described herein. The means comprises comprise documents, digital storage media, optical storage media, audio presentations, visual displays or the like, containing the information or instructions. For example, the communication medium may be a displayed web site, a kiosk, brochure, product label, package insert, advertisement, handout, public announcement audiotape, videotape, DVD, CD, computer-readable chip, computer-readable card, computer-readable disk, computer memory, or any combination thereof. Useful information includes one or more of (1) methods for promoting the health and wellness of animals and (2) contact information for the animal's caregivers to use if they have a question about the invention and its use. Useful instructions include techniques for using the probes, instructions for performing a gene expression assay, and administration amounts and frequency for the substances. The communication means is useful for instructing on the benefits of using the invention.

EXAMPLES

Various aspects of the invention can be further illustrated by the following examples. It will be understood that these examples are provided merely for purposes of illustration and do not limit the scope of the invention disclosed herein unless otherwise specifically indicated.

Example 1

The physiological and biochemical effects of chronic oral OEA administration were investigated. Mice were chronically fed with OEA, provided as a supplement during 4 weeks, to study the effect on body weight gain and cumulative food intake, among other parameters.

Material and Methods

Animals, diet and experimental design. Adult male C3H mice purchased at 8 weeks of age were individually housed and maintained ad libitum on different diets and water for 2 weeks. Seven mice were allocated in 3 groups by randomization by weight, and fed with a high fat diet (lipids represented 50% of daily energy) during 2 weeks. The composition of the high fat diet per kg was: 284.5 g of corn starch, 89.5 g of saccharose, 250 g of casein, 50 g of cellulose, 10 g of a mix of vitamins (V1001), 35 g of a mix of minerals (S10026) and 281 g of canola oil (UPAE, Jouy en Josas, France). Then, OEA was added to the diets at different levels to provide 0, 10, or 100 mg OEA/kg body weight. The mice were kept on each respective diet for 4 weeks. During the nutritional intervention, daily food intake was monitored and the mice were weighed 3 times a week.

Sampling. At the end of the experimental period, mice were sacrificed by blood drawing after anesthesia with isoflurane. Plasma was obtained by centrifugation (1,000 g for 10 min at 4° C.). Mesenteric, epididymal, inguinal and peritoneal adipose depots, as well as liver, stomach, small intestine mucosa and gastrocnemian muscle were excised and frozen into liquid nitrogen. Plasma and organ samples were kept at −80° C. until analysis. Triglycerides, glucose, total cholesterol and HDL cholesterol were directly measured on plasma samples collected during the sacrifice by enzymatic procedures, using a Beckman Coulter Systems SYNCHRON LX 20 (Beckman Coulter, Fullerton, USA) (oxidase method, Beckman Coulter for glucose, GPO method, Beckman Coulter for TG, oxidase and esterase method, Beckman Coulter for cholesterol). HDL were isolated by specific solubilization, using a precipitation isolation kit (Beckman Coulter, Fullerton, USA).

Statistical analysis. Results were determined as mean±standard error of the mean (SEM). Statistical analysis of physiological parameters was performed by one-way ANOVA on Statview software (SAS institute, Cary, USA). Statistical significance was set up at the $P<0.05$ level.

Results

Food intake. According to linear regression analysis, cumulative food intake over the experimental period could predict up to 40% of the total variation of the adipose fat pad masses. Food intake was slightly (−6.5%) but significantly ($P<0.05$) decreased in mice consuming OEA. Daily food intake was significantly different for both doses of OEA compared with control all over the experimental period (two ways ANOVA, $P<0.01$). However, the observed effect was not dose dependent.

Physiological and biochemical parameters. OEA treatment did not induce hepatomegaly. OEA induced a similar decrease of total adipose fat pads weight. Peritoneal adipose tissue was mainly decreased, and the inguinal fat pads, taken as an indicator of the subcutaneous fat depot (main site of fat storage), were also decreased by OEA intake ($P<0.05$), whereas the mesenteric fat pads remained unaffected independently of the dose administrated. The final body weight of the mice was not affected.

Plasma triglycerides were significantly lowered in both OEA groups (−72%, $P<0.05$ for the 10 mg dose; −59%, $P<0.05$ for the 100 mg dose). A trend to decreased plasma total cholesterol was observed at 10 mg/kg, which reached statistical significance at the 100 mg/kg body weight treatment.

Example 2

The expression of 45 genes was measured by real-time PCR in peripheral tissues to identify genes that were differentially expressed in response to oral administration of oleoylethanolamide (OEA) or a non-hydrolysable OEA analog (KDS 5104), which affect satiety, lipid metabolism, fat utilization, food intake, and body fat mass.

Materials and Methods

Animals, diet, and experimental design. Adult male C57bl6j mice purchased at 8 weeks of age were individually housed and maintained ad libitum on high fat diet and water for 2 weeks. Seven mice were randomly allocated in 3 groups and fed with a high fat diet (lipids represented 50% of daily energy) for 2 weeks. For one kilogram, the composition of the high fat diet was: 235 g casein, 201 g saccharose, 3.5 g L-cystine, 85 g starch, 116 g maltodextrin, 60 g cellulose, 12 g vitamins mix (AIN-93M, UPAE, Jouy-en-Josas, France), 51.5 g mineral mix (AIN-93Vx, UPAE, Jouy-en-Josas, France), and 236 g lard. Then, either OEA or KDS 5104 was added to the diet at a concentration of 100 mg/kg/body weight. The mice were kept under treatment for 5 weeks.

Chemical synthesis. OEA was chemically synthesized from high oleic sunflower oil and ethanolamine (Sigma-Aldrich, Saint-Louis, USA) according to Roe, E T et al, 1952, J. American Oil Chemists' Society 29 (1): 18-22. KDS 5104 [(Z)—(R)-9-octadecenamide, N-(2-hydroxyethyl, 1-methyl)] was synthesized by the stoichiometric reaction of oleoylchloride with the corresponding amine: (R)-(−)-2-aminopropanol (Sigma-Aldrich, Saint-Louis, USA) in the presence of triethylamine (Sigma-Aldrich, Saint-Louis, USA) using known procedures. The reaction was conducted in dichloromethane at 0-4° C. under stirring for 12 h. The solvent was removed under vacuum, and the mixture was dissolved in tetrahydrofuran/ethanol (1:1) and treated with an aqueous solution of 3 N KOH (2 Eq). The solution was kept at reflux for 30 min, after which the solvent was removed. The residue was dissolved in ethyl acetate and washed sequentially with water, sodium hydroxide (2 N), hydrochloric acid (2 N), and brine. The organic phase was dried over sodium sulfate, filtered, and concentrated under reduced pressure (cf. Astarita et al, 2006, J. Pharmacol. Exp. Ther. 318 (2): 563-70).

Sampling. At the end of the experimental period, mice were sacrificed by blood drawing (cardiac puncture) after anesthesia with isoflurane. Plasma was obtained by centrifugation (1,000 g for 10 min at 4° C.). Mesenteric, epididymal, inguinal and peritoneal adipose depots, as well as liver, stomach, small intestine mucosa, pancreas, and gastrocnemian muscle were removed and frozen into liquid nitrogen. Plasma, urine, feces, and organ samples were kept at −80° C. until analysis.

RNA extraction and gene expression. Total RNA from liver, intestine mucous membrane, adipose tissues, gastrocnemian muscle, pancreas and stomach were extracted with TRIzol reagent (Invitrogen, Carlsbad, USA) according to the manufacturer's instruction. The RNA concentration was determined on nanodrop from the absorbance at 260 nm. Retro-transcription PCRs to synthesize cDNA were performed using an Applied Biosystem Thermal Cycler 2720 and Superscript II (Invitrogen, Carlsbad, USA) according to manufacturer's protocol. Real-time quantitative PCR (RT-qPCR) were performed on cDNA obtained as described above using a high through put system (Biomek 3000, Beckman & Coulter, Fullerton, USA) and a Lightcycler 480 (Roche/Hitachi, Basel, Switzerland) with SYBR Green Master mix+kit (Eurogentec, Philadelphia, USA). Primers for the selected genes were generated using online informatics assistance from the Lightcycler manufacturer (Roche). Databases used to identify the genes were (1) the NCBI database (GenBank) and (2) the IHOP (Information Hyperlinked over Protein) database (www.ihop-net.org/UniPub/iHOP/bng/). Values were expressed as ratio of RNA levels relative to control mice (diets with 0 mg of OEA/kg/body weight) using $\Delta\Delta(Ct)$ (Livak K J & Schmittgen T D, 2001, Methods 25:402-8). Gene expression of the following genes was measured (abbreviation and GenBank Accession shown in parentheses).

AcylCoA oxidase (ACO) (NM_015729)
Peroxisome proliferator activated receptor gamma coactivator 1 alpha (PGC 1α) (NM_008904)
Phosphoenolpyruvate carboxykinase (PEP CK) (NM_028994)
Peroxisome proliferator activated receptor alpha (PPAR α) (NM_011144)
Peroxisome proliferator activated receptor gamma (PPAR γ) (NM_133249)
Acyl CoA carboxylase (ACC) (NM_133360)
Fasting induced adipocyte factor (Fiaf) (NM_020581)
Fatty acid transporter/cluster of differentiation 36 (FAT/CD 36) (NM_007643)
Lipoprotein lipase (LPL) (NM_008509)
Liver fatty acid binding protein 1 (LFABP 1) (NM_017399)
Protein convertase subtilisin/kexin type 9 (PCSK 9) (NM_153565)
A disintegrin and metalloproteinase domain 17 (Adam 17) (NM_009615)
Ghrelin (NM_021488)
G protein coupled receptor 119 (GPR 119) (NM_181751)
Cholescystokinin (CCK) (NM_031161)
Peptide YY (PYY) (NM_145435)
Leptin (NM_008493)
Adiponectin (NM_009605)
Visfatin (NM_021524)
Sterol regulatory element binding protein-c 1 (SREBP 1c) (NM_011480)
Sterol regulatory element binding protein-C 2 (SREBP2 1) (NM_033218)
Fatty acid amide hydrolase (FAAH) (NM_010173)
N-acylsphingosine amidohydrolase-like (NAAA) (NM_025972)
Oleoylethanolamide synthase (OEA synthase) (NM_178728)
Uncoupling protein 2 (UCP2) (NM_011671)
Glucose transporter 4 (Glut 4) (NM_009204)
Peroxisome proliferator activated receptor delta (PPAR □) (NM_011145)
Cannabinoid receptor 1 (CB 1) (NM_007726)
Insulin receptor substrate 1 (IRS 1) (NM_010570)
Glucose 6-phosphatase (G6P) (NM_008061)
Stearoyl-Coenzyme A desaturase 1 (SCD 1) (NM_009127)
Fatty Acid Synthase (FAS 1) (NM_007988)

Statistical analysis. Results are presented as means±standard error of the means (SEM). Statistical analysis of physiological parameters and gene expression data was performed by one-way ANOVA on Statview software (SAS Institute, Cary, USA). Daily food intake was analyzed using two-way ANOVA on Statview software. Statistical significance was set up at the $P<0.05$ level, the $P<0.01$ level and the $P<0.001$ level. For statistical analysis of the gene expression data, values were calculated relative to 18S expression for each mouse and gene.

Results

The results for the OEA treatment are shown in Table 1. The results for the KD5104 treatment are shown in Table 2. The following nomenclature is used in the Tables: i: proximal intestine, s: stomach, l: liver, m: muscle, p: pancreas; at: adipose tissue, at ep: epidydimal adipose tissue; at per: peritoneal adipose tissue.

TABLE 1

| FUNCTIONS | GENES | All Genes | Group A 0.05 < P value < 0.01 | Group B 0.01 < P value < 0.001 | Group C P value < 0.001 |
|---|---|---|---|---|---|
| Lipid β-oxidation | CPT1 p | 1.35 | | | |
| | CPT1 l | | | 1.74 | |
| | CPT1 i | | 2.00 | | |
| | ACO l | 1.06 | | | |
| | UCP2 m | 1.19 | | | |
| Lipogenesis | FAS l | | | | 1.65 |
| | SREBP1c l | | 1.24 | | |
| | SREBP1c at ep | 1.08 | | | |
| | SREBP1c at per | −1.39 | | | |
| | SREBP2 l | 1.22 | | | |
| | SCD1 l | | | −2.13 | |
| | SCD 1 at ep | 1.00 | | | |
| | SCD 1 at per | −1.30 | | | |
| Lipid transport | FAT/CD36 l | | | 1.45 | |
| | FAT/CD36 i | | | 1.61 | |

TABLE 1-continued

| FUNCTIONS | GENES | All Genes | Group A 0.05 < P value < 0.01 | Group B 0.01 < P value < 0.001 | Group C P value < 0.001 |
|---|---|---|---|---|---|
| | FAT/CD36 at ep | | | −1.88 | |
| | FAT/CD36 at per | | −1.81 | | |
| | PCSK9 l | | | 1.44 | |
| | Fiaf i | 1.15 | | | |
| | Fiaf at ep | | −1.41 | | |
| | Fiaf at per | | | −2.42 | |
| Insulin signaling | visfatin at ep | | | | −1.55 |
| | visfatin at per | | | | −1.80 |
| | adiponectin at ep | −1.14 | | | |
| | adiponectin at per | | | −2.08 | |
| Food intake control | ghrelin s | | | 1.98 | |
| | GPR119 i | | | | 1.97 |
| | PPAR α i | 1.20 | | | |
| | CCK i | | | 1.57 | |
| | leptin at ep | 1.22 | | | |
| | leptin at per | | 3.44 | | |
| | leptin s | 1.41 | | | |
| Fatty Acid Ethanolamides metabolism and signaling | CB1 i | −1.02 | | | |
| | CB1 at ep | | −1.94 | | |
| | CB1 at per | | | −5.27 | |
| | FAAH i | | | 1.68 | |
| | FAAH at ep | | | 2.22 | |
| | FAAH at per | | 1.62 | | |
| | NAAA i | | | 1.85 | |
| | NAAA at ep | | 1.36 | | |
| | NAAA at per | 1.03 | | | |
| | OEA synthase i | | | −1.38 | |
| Glucose metabolism | Glut 4 m | | | 3.27 | |
| | PepCK l | 1.02 | | | |
| | G6P l | | 1.29 | | |

Referring to Table 1, multivariate statistical analysis showed a significant shift in the overall gene expression pattern upon OEA treatments. The genes of adipose leptin and FAAH (fatty acid amide hydrolase), intestinal FAT/CD36 and OEA receptor GPR119 were among the genes mainly responsible for this shift, and were also associated with reduced body fat pads. Adipose FAAH was found to be mainly associated with a decrease in food intake. These data show that anti-obesity action of OEA relies partly on the modulation of the fatty acid amides hydrolysis pathway in the adipose tissue and through the modulation of the newly discovered GPR119 OEA signaling pathway and fatty acid uptake regulation in the proximal intestine.

TABLE 2

| FUNCTIONS | GENES | All Genes | Group A 0.05 < P value < 0.01 | Group B 0.01 < P value < 0.001 | Group C P value < 0.001 |
|---|---|---|---|---|---|
| Lipid β-oxidation | CPT1 p | | | 1.80 | |
| | CPT1 l | 1.06 | | | |
| | CPT1 i | | | | 1.63 |
| | ACO l | 1.15 | | | |
| | UCP2 m | 1.11 | | | |
| Lipogenesis | FAS l | | | | 2.47 |
| | SREBP1c l | | | 1.47 | |
| | SREBP1c at ep | 1.00 | | | |
| | SREBP1c at per | −1.35 | | | |
| | SREBP2 l | 1.13 | | | |
| | SCD1 l | | | −1.91 | |
| | SCD 1 at ep | 1.24 | | | |
| | SCD 1 at per | 1.51 | | | |
| Lipid transport | FAT/CD36 l | 0.88 | | | |
| | FAT/CD36 i | | | | 1.83 |
| | FAT/CD36 at ep | | −2.24 | | |
| | FAT/CD36 at per | 1.01 | | | |
| | PCSK9 l | | | 1.34 | |
| | Fiaf i | | | | 0.68 |
| | Fiaf at ep | | | | 0.46 |
| | Fiaf at per | | | | 2.79 |
| Insulin signaling | visfatin at ep | −1.08 | | | |
| | visfatin at per | −1.10 | | | |
| | adiponectin at ep | −1.02 | | | |
| | adiponectin at per | | | −1.52 | |
| Food intake control | ghrelin s | 1.04 | | | |
| | GPR119 i | | | | 4.95 |

TABLE 2-continued

| FUNCTIONS | GENES | All Genes | Group A 0.05 < P value < 0.01 | Group B 0.01 < P value < 0.001 | Group C P value < 0.001 |
|---|---|---|---|---|---|
| | PPAR a i | 1.02 | | | |
| | CCK i | | | 1.62 | |
| | leptin at ep | 1.35 | | | |
| | leptin at per | −1.32 | | | |
| | leptin s | −1.02 | | | |
| Fatty Acid Ethanolamides metabolism and signaling | CB1 i | −1.25 | | | |
| | CB1 at ep | −1.48 | | | |
| | CB1 at per | | −3.00 | | |
| | FAAH i | 1.28 | | | |
| | FAAH at ep | | | 9.71 | |
| | FAAH at per | | | 3.82 | |
| | NAAA i | | | | 1.60 |
| | NAAA at ep | | 1.38 | | |
| | NAAA at per | | 1.52 | | |
| | OEA synthase i | | −1.36 | | |
| Glucose metabolism | Glut 4 m | | | | 5.70 |
| | PepCK l | | | 1.55 | |
| | G6P l | | | 2.12 | |

Referring to Table 2, multivariate statistical analysis showed a significant shift in the overall gene expression pattern upon KDS 5104 treatments. The genes of liver FAS (Fatty Acid Synthase), intestinal CPT1 and oleoylethanolamide receptor GPR119 were among the genes mainly responsible for this shift, and were also associated with reduced body fat pads. Intestinal GPR119 was found to be mainly associated with a decrease in food intake. The data show that anti-obesity action of KDS 5104 partly relies on the modulation of the fatty acid amides hydrolysis pathway in the adipose tissue and through the modulation of the newly discovered GPR119 endocannabinoïd signaling pathway and fatty acid uptake regulation in the proximal intestine.

The specification has disclosed and exemplified typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

What is claimed is:

1. A combination comprising two or more chemically synthesized or chemically modified polynucleotides that specifically hybridize to two or more target polynucleotides that are differentially expressed in animals exhibiting a phenotype comprising a decrease in body fat and plasma triglycerides and an increase in satiety as measured by decreased food intake (RBF/IS phenotype) resulting from extended regular ingestion of a substance that affects one or more of food intake, satiety, lipid metabolism, and fat utilization, the target polynucleotide comprising a gene selected from genes encoding proteins FAS, visfatin, or GPR119.

2. The combination of claim 1, further comprising two or more chemically synthesized or chemically modified polynucleotides that specifically hybridize to two or more target polynucleotides selected from genes encoding proteins CPT1, FAT/CD36, CB1, FAAH, NAAA, G6P, SREBP1c, Fiaf, leptin or PSK9.

3. The combination of claim 1, further comprising two or more chemically synthesized or chemically modified polynucleotides that specifically hybridize to two or more target polynucleotides selected from genes encoding proteins SCD1, FAT/CD36, Fiaf, adiponectin, CCK, CB1, FAAH, NAAA, Glut4, CPT1, SREBP1c, PSK9, ghrelin, OEA synthase or KDS synthase.

4. The combination of claim 1, further comprising one or more chemically synthesized or chemically modified polynucleotides that specifically hybridize to one or more target polynucleotides selected from genes encoding proteins CPT1, ACO, and UCP2.

5. The combination of claim 1, further comprising one or more chemically synthesized or chemically modified polynucleotides that specifically hybridize to one or more target polynucleotides selected from genes encoding proteins SREBP1c, SREBP2, and SCD1.

6. The combination of claim 1, further comprising one or more chemically synthesized or chemically modified polynucleotides that specifically hybridize to one or more target polynucleotides selected from genes encoding proteins FAT/CD36, PCSK9, and Fiaf.

7. The combination of claim 1, further comprising a chemically synthesized or chemically modified polynucleotide that specifically hybridizes to a target polynucleotide from a gene encoding adiponectin.

8. The combination of claim 1, further comprising one or more chemically synthesized or chemically modified polynucleotides that specifically hybridize to one or more target polynucleotides selected from genes encoding proteins ghrelin, PPAR alpha, CCK, and leptin.

9. The combination of claim 1, further comprising one or more chemically synthesized or chemically modified polynucleotides that specifically hybridize to one or more target polynucleotides selected from genes encoding proteins CB1, FAAH, NAAA, and OEA synthase.

10. The combination of claim 1, further comprising one or more chemically synthesized or chemically modified polynucleotides that specifically hybridize to one or more target polynucleotides selected from genes encoding proteins Glut4, PepCK, and G6P.

11. The combination of claim 1 wherein the substance is a fatty acid amide.

12. The combination of claim 11 wherein the substance is N-oleoyl-ethanolamide or a hydrolysis-resistant derivative thereof.

13. The combination of claim 12 wherein the substance is (Z)-(R)-9-octadecenamide, N-(2-hydroxyethyl, 1-methyl).

14. A composition comprising two or more probes for detecting differential gene expression in animals exhibiting a phenotype comprising a decrease in body fat and plasma triglycerides and an increase in satiety as measured by decreased food intake (RBF/IS phenotype) resulting from extended regular ingestion of a substance that affects one or more of food intake, satiety, lipid metabolism, and fat utilization, wherein the probes comprise:
 a) chemically modified polynucleotides that specifically hybridize to two or more genes encoding proteins FAS, visfatin, or GPR119; or
 b) polypeptide binding agents that specifically bind to two or more polypeptides selected from proteins FAS, visfatin, or GPR119.

15. The composition of claim 14 wherein the polypeptide binding agents are antibodies.

16. A device comprising a solid support to which is affixed an array comprising a plurality of probes for detecting differential gene expression in animals exhibiting a phenotype comprising a decrease in body fat and plasma triglycerides and an increase in satiety as measured by decreased food intake (RBF/IS phenotype) resulting from extended regular ingestion of a substance that affects one or more of food intake, satiety, lipid metabolism, and fat utilization, wherein the probes comprise:
 a) polynucleotides that specifically hybridize to two or more genes encoding proteins FAS, visfatin, or GPR119; or
 b) polypeptide binding agents that specifically bind to two or more polypeptides selected from proteins FAS, visfatin, or GPR119.

17. The device of claim 16 wherein the polypeptide binding agents are antibodies.

* * * * *